(12) United States Patent
Sakai

(10) Patent No.: US 10,697,865 B2
(45) Date of Patent: Jun. 30, 2020

(54) PREPROCESSING APPARATUS FOR GAS ANALYSIS

(71) Applicant: Japan Agency for Marine-Earth Science and Technology, Yokosuka-shi, Kanagawa (JP)

(72) Inventor: Saburo Sakai, Yokosuka (JP)

(73) Assignee: JAPAN AGENCY FOR MARINE-EARTH SCIENCE AND TECHNOLOGY, Yokosuka-Shi (JP)

( * ) Notice: Subject to any disclaimer, the term of this patent is extended or adjusted under 35 U.S.C. 154(b) by 202 days.

(21) Appl. No.: 15/757,184

(22) PCT Filed: Sep. 6, 2016

(86) PCT No.: PCT/JP2016/076107
§ 371 (c)(1),
(2) Date: Mar. 2, 2018

(87) PCT Pub. No.: WO2017/043468
PCT Pub. Date: Mar. 16, 2017

(65) Prior Publication Data
US 2018/0252620 A1 Sep. 6, 2018

(30) Foreign Application Priority Data
Sep. 8, 2015 (JP) .................. 2015-176635

(51) Int. Cl.
*G01N 1/00* (2006.01)
*G01N 1/22* (2006.01)
(Continued)

(52) U.S. Cl.
CPC ............ *G01N 1/2226* (2013.01); *G01N 1/00* (2013.01); *G01N 1/22* (2013.01); *G01N 30/12* (2013.01);
(Continued)

(58) Field of Classification Search
CPC .......... G01N 1/22; G01N 30/12; G01N 30/20; G01N 31/00
See application file for complete search history.

(56) References Cited

U.S. PATENT DOCUMENTS

2002/0017909 A1\* 2/2002 Tsuda .................. G01N 30/30
324/713
2014/0318217 A1\* 10/2014 Li ...................... G01N 33/0016
73/23.41

FOREIGN PATENT DOCUMENTS

EP 2316020 5/2011
JP 2001-318007 A 11/2001
(Continued)

OTHER PUBLICATIONS

European Search Report dated May 7, 2019, 9 pages.
(Continued)

*Primary Examiner* — Jamel E Williams
(74) *Attorney, Agent, or Firm* — Rankin, Hill & Clark LLP

(57) ABSTRACT

Provided herein is a preprocessing apparatus for gas analysis that enables preprocessing for gas analysis to be performed without requiring a cryogen. A preprocessing apparatus for gas analysis 101 mainly includes a gas flow path 103, a cooling portion 105, and a plurality of valves V101 to V105 that serve as gas flow path connection changing means for changing the gas flow path. The cooling portion 105 is operable to cool the collecting portion 113, and is constituted from a heat conductor 121, a cooling device 127, and a sealed structure 129. The cooling device 127 can cooled a contact cooling section 131 to an extremely low temperature by utilizing electrical energy. The cooling device 127 is used to bring the collecting portion 113 to a first temperature at which the target gas to be analyzed is solidified, and to thereafter bring the collecting portion 113 to a second
(Continued)

temperature at which only the target gas to be analyzed is gasified. By performing such processes, the target gas to be analyzed can be extracted by removing gases of impurities from a mixed gas.

19 Claims, 10 Drawing Sheets

(51) Int. Cl.
*G01N 31/00* (2006.01)
*G01N 30/12* (2006.01)
*G01N 30/20* (2006.01)
*G01N 33/00* (2006.01)
*G01N 30/02* (2006.01)

(52) U.S. Cl.
CPC ............ *G01N 30/20* (2013.01); *G01N 31/00* (2013.01); *G01N 33/0047* (2013.01); *G01N 2030/025* (2013.01); *G01N 2030/121* (2013.01)

(56) References Cited

FOREIGN PATENT DOCUMENTS

| JP | 2002-340755 | A | 11/2002 | |
|----|----|----|----|----|
| JP | 2003-066019 | A | 3/2003 | |
| JP | 2004-212075 | A | 7/2004 | |
| JP | 2014-529080 | A | 10/2014 | |
| WO | WO-2010004404 | A1 * | 1/2010 | ............ G01N 30/12 |

OTHER PUBLICATIONS

Barron, "Cryogenic Heat Transfer" Dec. 31, 1999, CRC Press, XP002790845, pp. 52-54.
Matsuhisa, "Oxygen and Hydrogen Isotope Geology (1)", Geological News, Feb. 1978 Issue, No. 282, 9 pages.
Isoprime, "Carbonate Analysis on the MultiCarb Dual-Inlet System", (http://www.isoprime.co.uk/files/TN010.pdf), 1 page.
Kasama, et al., "Analysis of Minute Amount of Volatile Component by P&T-GC/MS Method", Nichias Technical Report, No. 328, June Issue, 2001, 7 pages.

* cited by examiner

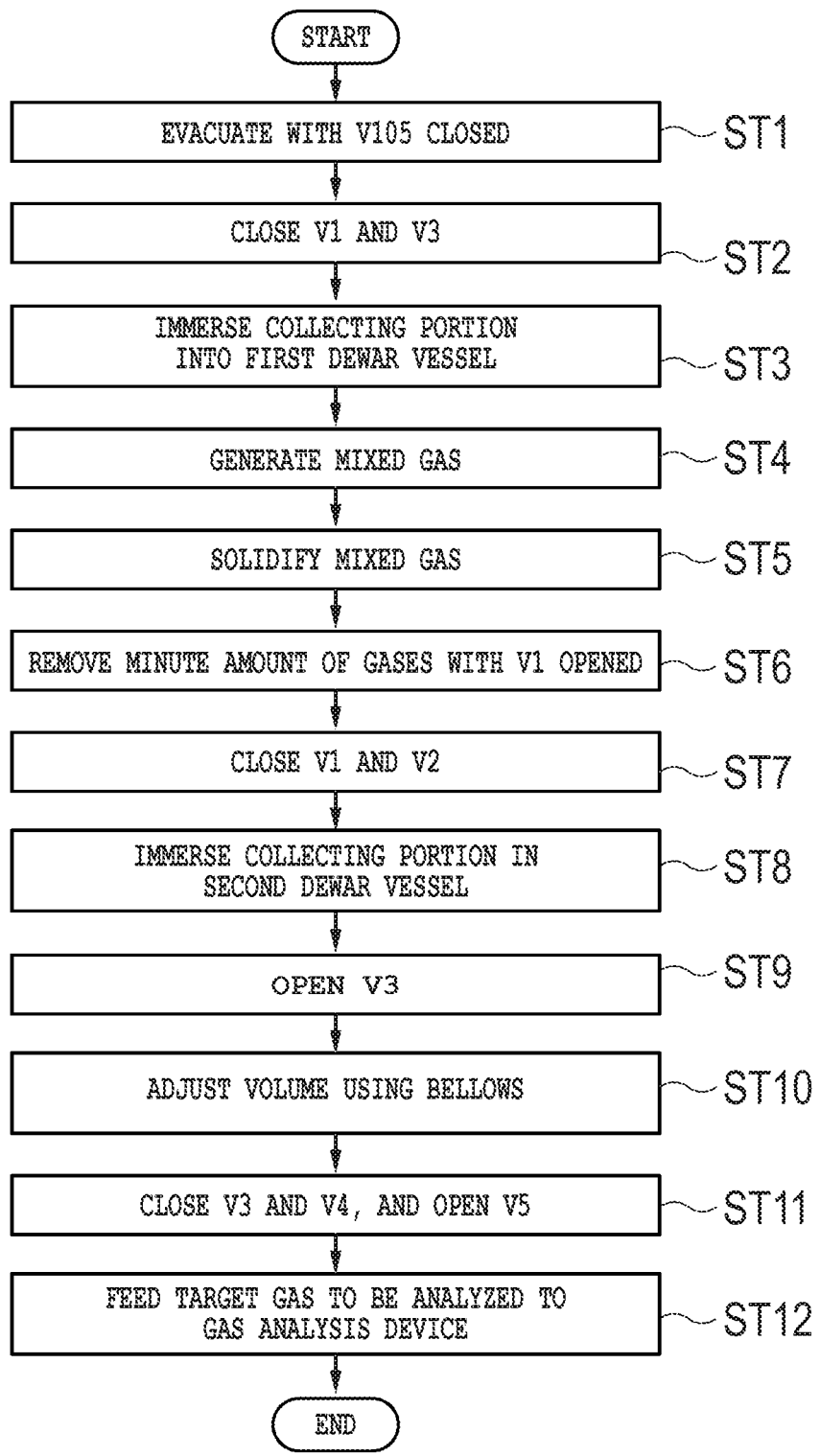

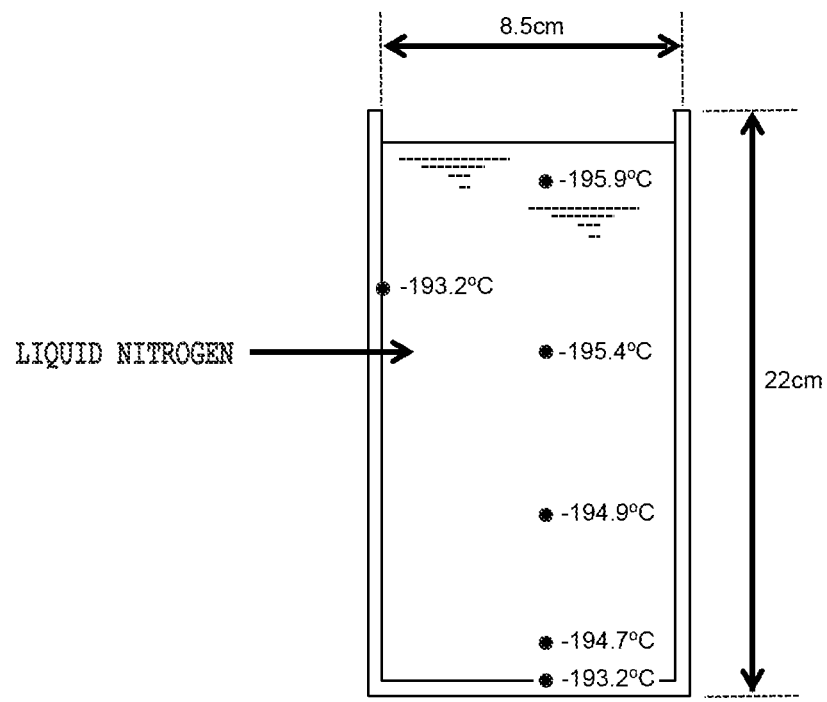

PREPROCESSING APPARATUS FOR GAS ANALYSIS

TECHNICAL FIELD

The present invention relates to a preprocessing apparatus for gas analysis operable to introduce a target gas to be analyzed into a gas analysis device.

BACKGROUND ART

Mass spectrometers and gas analysis devices such as a laser isotope spectroscopic measurement device that uses laser spectrometry have been put into practical use. FIG. 9 is a schematic diagram illustrating an example configuration of a preprocessing apparatus for gas analysis according to the related art. A preprocessing apparatus 1 for gas analysis separates a target gas to be analyzed and gases of impurities from a mixed gas, and introduces the target gas into a gas analysis device. The preprocessing apparatus 1 for gas analysis mainly includes a gas flow path 3, a cooling portion 5, and a plurality of valves V1 to V5 that serve as gas flow path connection changing means for changing the gas flow path. The gas flow path 3 is constituted from a glass pipe having a pipe diameter of 1 cm to 1.5 cm, and connected to a gas generating source 7, a vacuum pump 9, and a gas analysis device 11 via the valves. A collecting portion 13 configured to collect the gases of impurities is provided in the gas flow path 3 between the valves V2 and V3. A bellows 15 and a pressure gauge 17 are provided between the collecting portion 13 and the gas analysis device 11. The target gas is introduced into the gas analysis device 11 at a constant pressure by the bellows 15.

The cooling portion 5 cools the collecting portion 13, and is formed from a Dewar vessel 19 and a cryogen put in the Dewar vessel 19.

In a conventional example, the gas generating source 7 is configured such that phosphoric acid can be dropped into a container that contains a sample. Phosphoric acid is dropped onto the sample to generate a mixed gas. In this example, shells or a part of bones containing calcium carbonate ($CaCO_3$) are used as the sample. When phosphoric acid is dropped onto the sample, a mixed gas containing carbon dioxide ($CO_2$), water ($H_2O$), and a minute amount of other gases is generated. $CO_2$ is the target gas to be analyzed. $H_2O$ (and the minute amount of other gases) is the gas of impurities. As a matter of course, the gas generating source 7 may cause a reaction between a different sample and a different substance. Outside air may be directly introduced to analyze a target gas contained in the air. The vacuum pump 9 evacuates the gas flow path 3 to establish a vacuum (low to middle vacuum) state.

The collecting portion 13 is formed by shaping a glass pipe into a U-shape or a spiral shape, and immersed in the cryogen put in the Dewar vessel 19 for cooling.

FIG. 10 is a flowchart according to the related art of a process in which the target gas to be analyzed is introduced into the gas analysis device 11. To introduce the target gas into the gas analysis device 11, first, the gas flow path 3 is evacuated using the vacuum pump 9, with only the valve V5 being closed, to establish a vacuum (low to middle vacuum) state (step ST1). Then, the valves V1 and V3 are closed (step ST2), and the collecting portion 13 is immersed in a first Dewar vessel 19A filled with liquid nitrogen (at about −196° C.) which serves as a first cryogen (step ST3). When the gas generating source 7 generates a gas (mixed gas) (step ST4), a pressure gradient is caused between the gas generating source 7 and the collecting portion 13 which has been cooled by the liquid nitrogen, and the generated mixed gas is collected in the collecting portion 13 and solidified (step ST5). Specifically, $CO_2$ is solidified into dry ice, and $H_2O$ is solidified into ice. The minute amount of other gases that cannot be collected at this point is removed utilizing the vacuum pump 9 with the valve V1 being opened (step ST6). After that, the valves V1 and V2 are closed (step ST7).

Next, the first Dewar vessel 19A is replaced with a second Dewar vessel 19B filled with a second cryogen (at about −80° C.) prepared by adding ethanol to liquid nitrogen (step ST8). Then, the temperature of the collecting portion 13 is gradually raised to about −80° C., and $CO_2$ alone is gasified with $H_2O$ remaining ice. After that, the valve V3 is opened (step ST9) to measure the amount of generated $CO_2$ using the pressure gauge 17. The volume of the bellows 15 is adjusted so as to establish a predetermined pressure (step ST10). The valves V3 and V4 are closed, and the valve V5 is opened (step ST11). The target gas to be analyzed is diffused or scattered to feed the target gas to the gas analysis device (step ST12).

The foregoing is a common method of preprocessing performed before the target gas to be analyzed is introduced into the gas analysis device (see Non-Patent Document 1).

Recently, there has been proposed a device that also achieves the temperature of −80° C. by heating the collecting portion 13 using a heating wire, instead of replacing the first cryogen with the second cryogen (Non-Patent Document 2). In this device, a stainless steel pipe having a pipe diameter of about 0.6 cm is used for gas flow path.

In the "purge and trap" method which is used for volatile gas analysis, a sample set in a thermal desorption portion is heated under an inert gas (helium), a generated gas component is adsorbed by a trap pipe (collecting portion) that has been cooled. Next, the trap pipe is rapidly heated, and the adsorbed gas is introduced for gas chromatography or the like. The trap pipe (collecting portion) is cooled using liquid nitrogen (Non-Patent Document 3).

RELATED-ART DOCUMENT

Patent Documents

Non-Patent Document 1: "Oxygen and Hydrogen Isotope Geology (1)", by MATSUHISA Yukihiro, Geological News, February 1978 issue, No. 282

Non-Patent Document 2: "Carbonate Analysis on the MultiCarb Dual-Inlet System", by Isoprime, (http://www.isoprime.co.uk/files/TN010.pdf)

Non-Patent Document 3: "Analysis of Minute Amount of Volatile Component by P&T-GC/MS Method", by KASAMA Atsuko and HIRANO Takeshi, Nichias Technical Report, No. 328, June issue 2001

SUMMARY OF INVENTION

Technical Problem

The biggest problem with the method described in Non-Patent Document 1 is that a cryogen comprised of liquid nitrogen and a cryogen comprised of liquid nitrogen and ethanol must be used at room temperature. This is because the cryogen is gradually evaporated at room temperature and needs to be always replenished since the liquid surface in the Dewar vessel becomes lower if the cryogen is left as it is. According to a measurement by the inventor, as illustrated in FIG. 11, the temperature of the cryogen in the Dewar vessel (having a height of 22 cm and a diameter of 8.5 cm) tends to be higher at lower portions and on the outer side than at upper portions and on the inner side, respectively. Thus, it is difficult to keep the temperature of the liquid nitrogen constant. In addition, it is necessary to immerse the collecting portion 13 in the cryogen in the Dewar vessel 19, and therefore it is necessary to shape the collecting portion 13 so as to extend downward. The collecting portion 13 must have some degree of size since a glass pipe is used for the collecting portion 13. Further, in some cases, a concentration step is necessary to concentrate the target gas to be analyzed before the target gas is fed to the gas analysis device since the space in the glass pipe is large for the amount of the target gas to be analyzed, which makes the target gas thinner. Also in the concentration step, it is necessary to use liquid nitrogen as the cryogen. Further, when the Dewar vessel 19A is replaced with the Dewar vessel 19B, the glass pipe is exposed to room temperature, although only for a short time. Therefore, there is a risk that the mixed gas which has been solidified may be gasified, and quick replacement is required.

The device described in Non-Patent Document 2 does not require replacement of Dewar vessels. However, the device also uses liquid nitrogen as a cryogen, and therefore has the same issues as those of Non-Patent Document 1.

An object of the present invention is to provide a preprocessing apparatus for gas analysis that enables preprocessing for gas analysis to be performed without requiring a cryogen.

Another object of the present invention is to provide a preprocessing apparatus for gas analysis that obtains a target gas to be analyzed that has a sufficient concentration even without performing a step of concentrating the target gas to be analyzed.

Solution to Problem

A preprocessing apparatus for gas analysis according to the present invention includes, as basic components, a gas flow path including a collecting portion that is cooled in order to collect a target gas to be analyzed, and a cooling device operable to cool the collecting portion of the gas flow path. Further, a preprocessing apparatus for gas analysis, which separates the target gas from a mixed gas, includes: a gas flow path including a collecting portion that is cooled to a plurality of temperature levels in order to separate a target gas to be analyzed and gases of impurities from a mixed gas containing a plurality of kinds of gases; a cooling device operable to cool the collecting portion of the gas flow path to the plurality of temperature levels; and a gas flow path connection changing means for connecting the gas flow path to a vacuum pump when evacuating the gas flow path, connecting the gas flow path to a gas generating source when introducing the mixed gas into the gas flow path after the gas flow path has been evacuated, and connecting the gas flow path to a gas analysis device in order to supply the target gas, which has been separated by the collecting portion, to the gas analysis device. The collecting portion is cooled to a plurality of temperature levels according to the solidification temperature of the target gas. In general, the collecting portion is often cooled to a plurality of temperature levels in order to separate a gas having the lowest solidification temperature, as a target gas to be analyzed, from a mixed gas containing a plurality of kinds of gases and to collect other kinds of gases other than the target gas, as gases of impurities.

The preprocessing apparatus for gas analysis according to the present invention further includes a heat conductor configured to surround an outer periphery of the collecting portion. The cooling device includes a contact cooling section configured to contact the collecting portion to uniformly cool the collecting portion to a set temperature, and has a temperature adjusting function of adjusting a temperature of the contact cooling section to an arbitrary temperature by utilizing electrical energy. By using such a cooling device, it is possible to uniformly cool the entire collecting portion without using a cryogen such as liquid nitrogen, and to easily introduce the target gas to be analyzed into the gas analysis device. Since there is no need to use a cryogen, the direction of extension of the collecting portion is not limited, and it is not necessary to shape the collecting portion so as to extend downward as in the related art. The cooling device is specifically a stirling cooler.

In order to efficiently cool the collecting portion, the collecting portion, the heat conductor, and the contact cooling section may be received in a vacuum chamber of a sealed structure, the vacuum chamber being connected to a vacuum pump and evacuated; and the vacuum chamber may have been brought into a vacuum state by the vacuum pump when the collecting portion is cooled. With such a configuration, the collecting portion can be cooled without being affected by air or room temperature. In addition, if the heat conductor contacts the contact cooling section via an indium sheet, the collecting portion can be cooled more efficiently.

In order to stabilize the mixed gas which passes inside the collecting portion, the collecting portion is preferably meanderingly arranged in the heat conductor. Further, if the collecting portion is meanderingly arranged along a cooling surface of the contact cooling section, a larger portion of the collecting portion can be cooled by the contact cooling section, thereby efficiently cooling the collecting portion. Most suitably, the collecting portion has an overall length of 5 cm or more and 15 cm or less. The preprocessing apparatus for gas analysis according to the present invention does not need to use liquid nitrogen, and therefore does not need to use a glass pipe. Therefore, the collecting portion can have a diameter of one-eighth of an inch (3.175 mm) or less, and further one-sixteenth of an inch (1.5875 mm) or less.

If the collecting portion is a gas pipe, the heat conductor is preferably insert molded including the gas pipe as an insert. With such a configuration, the gas pipe and the heat conductor are unitarily formed, which enables the gas pipe as the collecting portion to be efficiently cooled.

The heat conductor may include a heater configured to be electrically energized to generate heat. With such a heater, the collecting portion which has been cooled by the cooling device can be heated, which enables quick temperature adjustment.

The preprocessing apparatus for gas analysis according to the present invention is used to introduce a target gas to be analyzed into a gas analysis device. For example, the preprocessing apparatus for gas analysis can be used to remove water ($H_2O$) as an impurity from a mixed gas generated by adding phosphoric acid to a sample and introducing carbon dioxide ($CO_2$) as a target gas into a gas analysis device. As a matter of course, however, the present invention is not limited thereto.

BRIEF DESCRIPTION OF DRAWINGS

FIG. 7 illustrates an example heat conductor including a heater, wherein

FIG. 10 is a flowchart of a conventional process until a target gas to be analyzed is introduced into a gas analysis device.

FIG. 11 illustrates the temperature distribution of liquid nitrogen in a Dewar vessel.

DESCRIPTION OF EMBODIMENTS

A preprocessing apparatus for gas analysis according to an embodiment of the present invention will be described in detail below with reference to the accompanying drawings.

Figure 1:
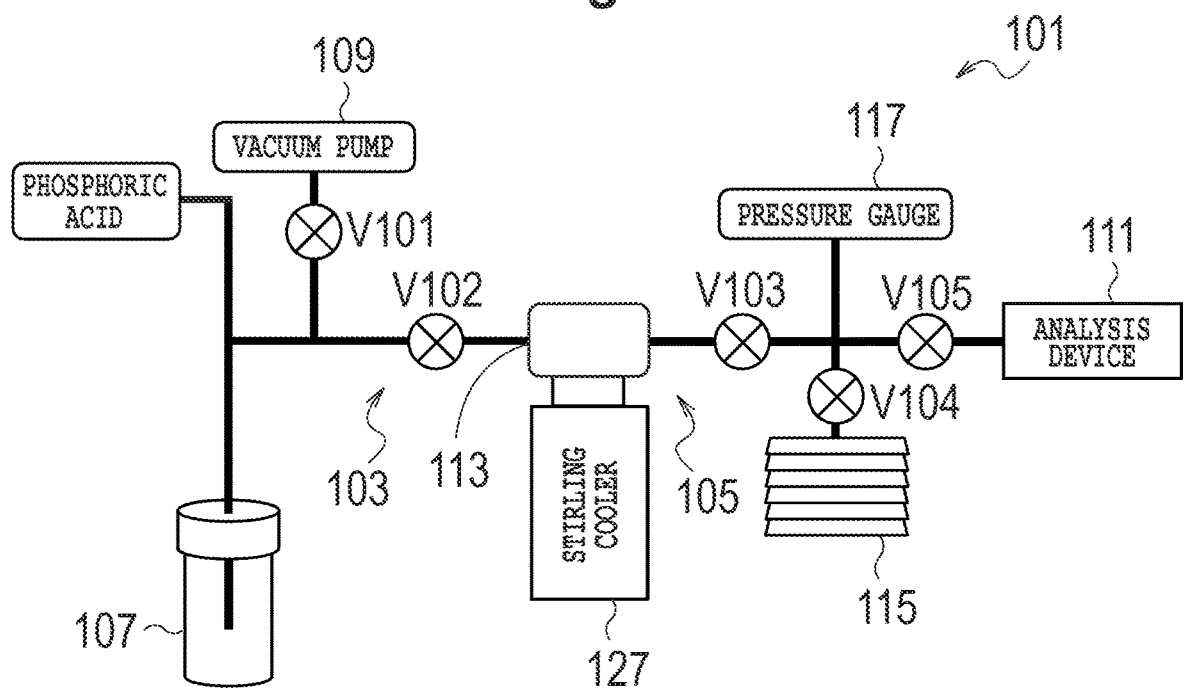
FIG. 1 is a schematic diagram illustrating an example configuration of a preprocessing apparatus for gas analysis according to an embodiment of the present invention.
Figure 2A:
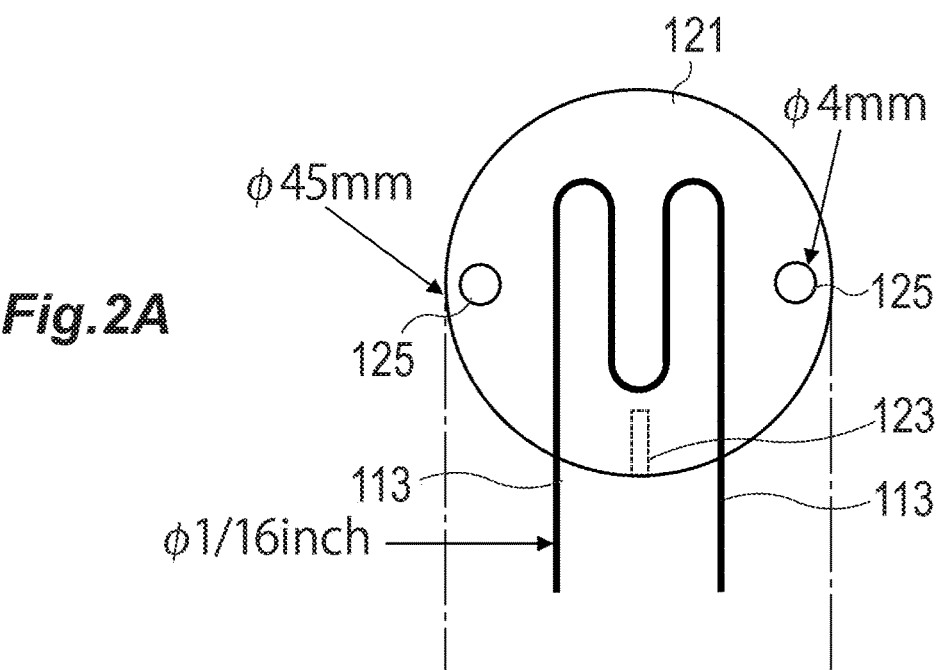
FIGS. 2A and 2B are a plan view and a front view, respectively, illustrating a collecting portion and a heat conductor with the heat conductor being rendered transparent.
Figure 2B:
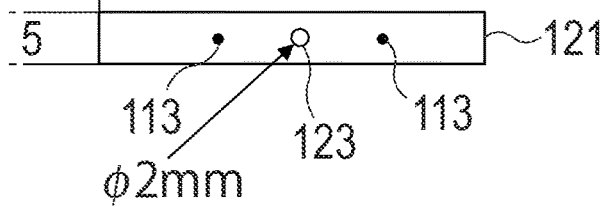
Figure 3:
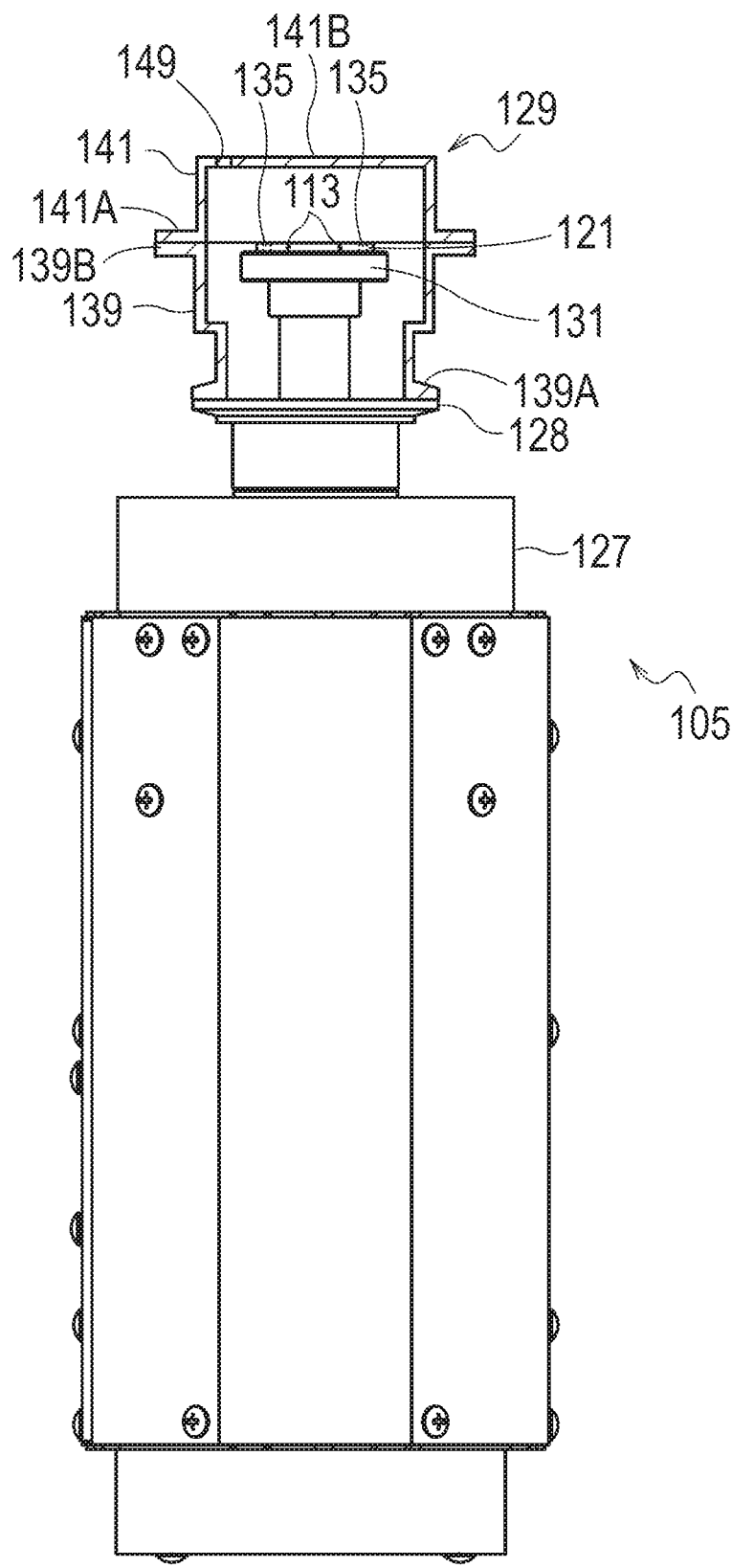
FIG. 3 is a front view illustrating the configuration of a cooling portion operable to cool the collecting portion.
Figure 4:
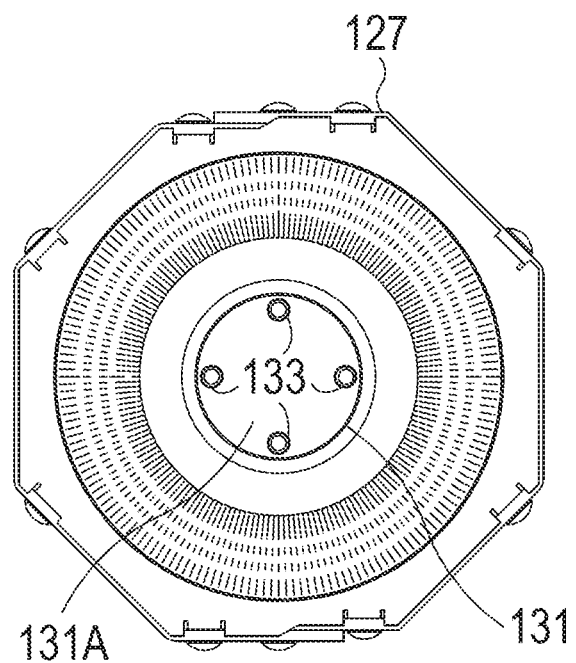
FIG. 4 is a plan view illustrating a contact cooling section of a cooling device.
Figure 5A:
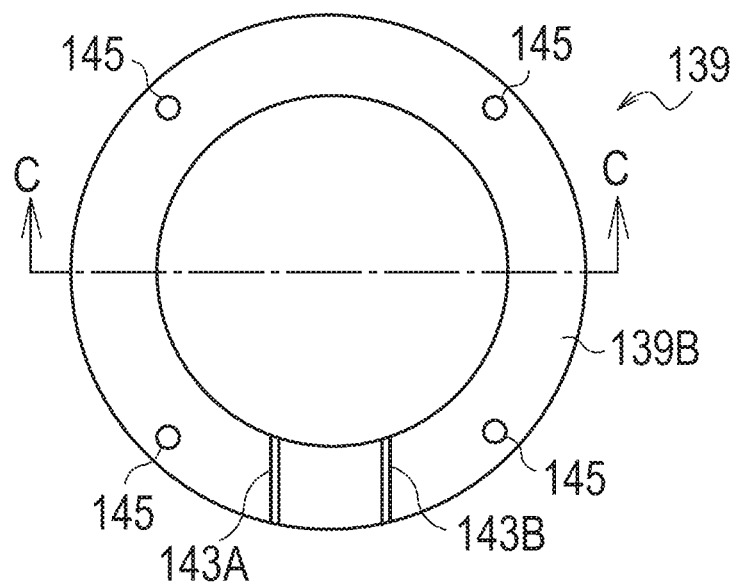
FIGS. 5A, 5B, and 5C are a plan view, a front view, and a sectional view taken along line C-C, respectively, of a lower structure forming a sealed structure.
Figure 5B:
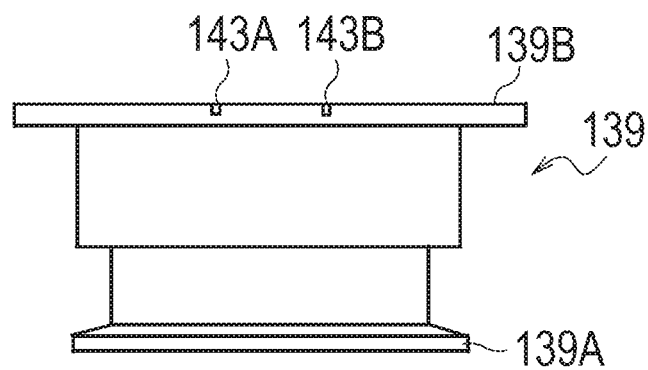
Figure 5C:
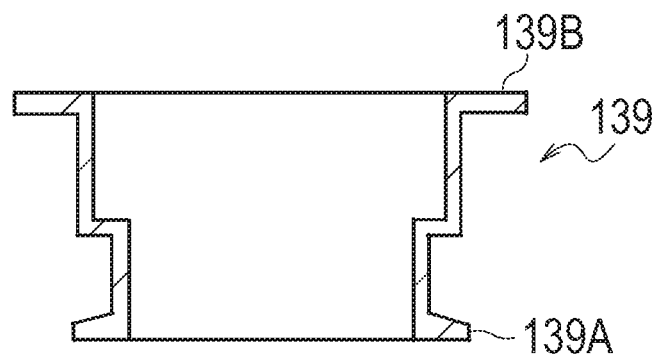
Figure 6A:
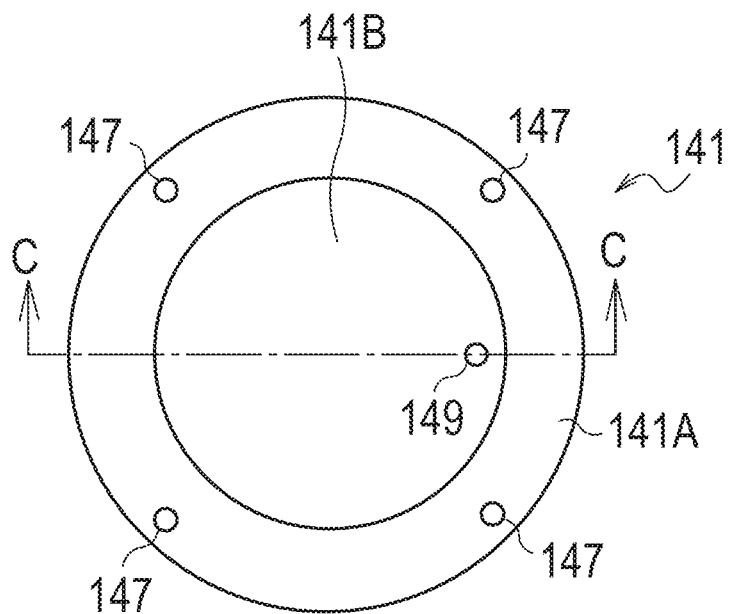
FIGS. 6A, 6B, and 6C are a plan view, a front view, and a sectional view taken along line C-C, respectively, of an upper structure forming the sealed structure.
Figure 6B:
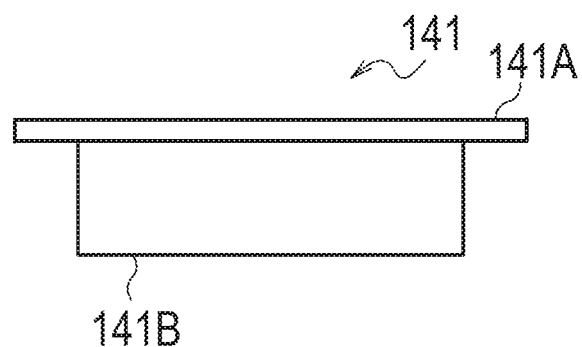
Figure 6C:
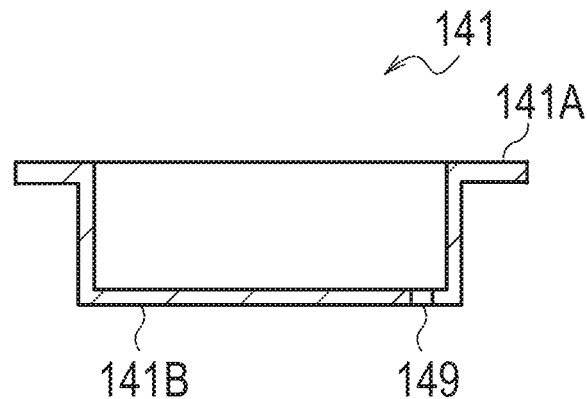

FIG. 1 is a schematic diagram illustrating the configuration of a preprocessing apparatus for gas analysis according to an embodiment. FIGS. 2A and 2B are a plan view and a front view, respectively, illustrating a collecting portion and a heat conductor with the heat conductor being rendered transparent. FIG. 3 is a front view illustrating the configuration of a cooling portion. FIG. 4 is a plan view illustrating a contact cooling section of a cooling device. FIGS. 5A, 5B, and 5C are a plan view, a front view, and a sectional view taken along line C-C, respectively, of a lower structure forming a sealed structure. FIGS. 6A, 6B, and 6C are a plan view, a front view, and a sectional view taken along line C-C, respectively, of an upper structure forming the sealed structure.

Figure 9:
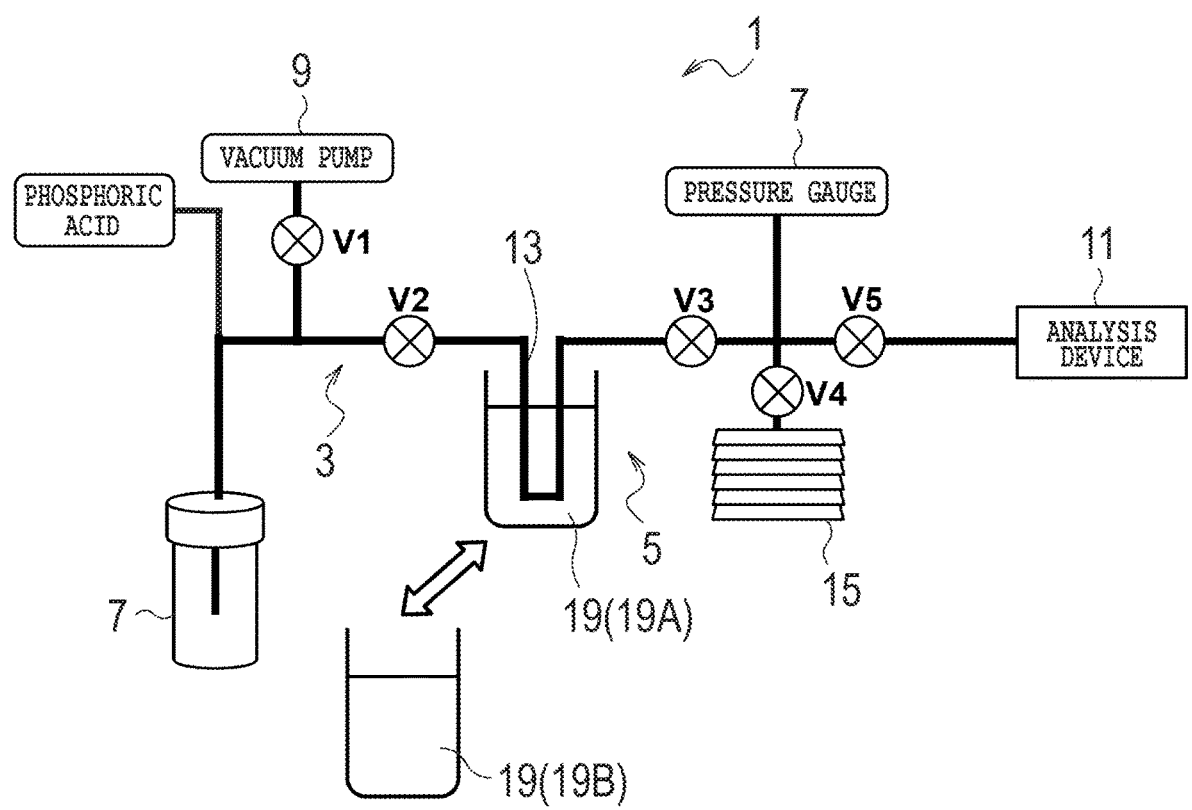
FIG. 9 is a schematic diagram illustrating the configuration of a conventional preprocessing apparatus for gas analysis.

As with the conventional preprocessing apparatuses for gas analysis, a preprocessing apparatus 101 for gas analysis mainly includes a gas flow path 103, a cooling portion 105, and a plurality of valves V101 to V105 that serve as gas flow path connection changing means for changing the gas flow path. The preprocessing apparatus 101 for gas analysis is different from the conventional preprocessing apparatus for gas analysis mainly in the configuration of a collecting portion 113 and the cooling portion 105 which cools the collecting portion 113. The preprocessing apparatus for gas analysis of the embodiment will be described below, focusing on the differences from the conventional preprocessing apparatuses for gas analysis. Common members are denoted by reference numerals obtained by adding 100 to the reference numerals affixed to their counterparts of the conventional preprocessing apparatus for gas analysis illustrated in FIG. 9, and explanations of such parts are occasionally omitted.

The gas flow path 103 of the embodiment is formed from a stainless steel alloy pipe having a pipe diameter of one-sixteenth of an inch (1.5875 mm) to one-eighth of an inch (3.175 mm), and connected to a gas generating source 107, a vacuum pump 109, and a gas analysis device 111 via valves. The gas flow path 103 includes a collecting portion 113 provided between the valves V102 and V103 and configured to collect gases of impurities. A bellows 115 and a pressure gauge 117 are provided between the collecting portion 113 and the gas analysis device 111. The target gas to be analyzed is introduced into the gas analysis device 111 at a constant pressure by the bellows 115.

[Collecting Portion and Heat Conductor]

The collecting portion 113 of the embodiment is a gas pipe made of a stainless steel alloy illustrated in FIG. 2. As the collecting portion, a pas pipe suitably has an overall length of 5 cm to 15 cm and a diameter of one-sixty-fourth of an inch (0.396875 mm) to one-eighth of an inch (3.175 mm). Use of such thin pipe having a small diameter can omit a step of concentrating the target gas to be analyzed, which is performed in the conventional method that uses a glass pipe having a large internal space. In gas chromatography, for example, which introduces a target gas into an analysis device using a carrier gas such as helium gas, a thin pipe having a small diameter, for example, of one-sixty-fourth of an inch (0.396875 mm) to one-sixteenth of an inch (1.5875 mm) is generally used for effective introduction or feeding of the target gas as with the embodiment of the present invention. The present invention can be directly applied to such devices. In the embodiment, the gas pipe has an overall length of 12 cm and a diameter of one-sixteenth of an inch (1.5875 mm). The outer periphery of the collecting portion 113 is surrounded by a heat conductor 121 made of a stainless steel alloy. The collecting portion 113 is meanderingly arranged in the heat conductor 121. In the embodiment, the heat conductor 121 is insert molded including the gas pipe, which is the collecting portion 113, as an insert. The heat conductor 121 has a temperature sensor insertion hole 123 formed therein for insertion of a temperature sensor configured to measure the temperature of the collecting portion 113. The heat conductor 121 also has through holes 125, 125 formed therein for fixation of the heat conductor 121 to a cooling device that will be discussed later. The dimensions of the respective portions are as illustrated in FIG. 2.

[Cooling Portion]

The cooling portion 105 is operable to cool the collecting portion 113, and is constituted from the heat conductor 121, a cooling device 127, and a sealed structure 129 as illustrated in FIG. 3. In FIG. 3, a lower structure 139 and an upper structure 141 of the sealed structure 129 are illustrated in section.

The cooling device 127 includes a disc-shaped contact cooling section 131 configured to contact the heat conductor 121 to uniformly cool the collecting portion 113 to a set temperature, and has a temperature adjusting function of adjusting the temperature of the contact cooling section 131 to an arbitrary temperature by utilizing electrical energy. In the embodiment, the cooling device 127 is specifically a stirling cooler operable to achieve an extremely low temperature through stirling cycles including constant-volume heating, isothermal expansion, constant-volume cooling, and isothermal compression. In the embodiment, more specifically, a "Cryo Cooler (model name: SC-UF01)" manufactured by Twinbird Corporation is used as the cooling device 127. SC-UF01 can bring the contact cooling section 131 to an extremely low temperature or a cryogenic temperature lower than −200° C. by utilizing electrical energy, and can finely control the temperature in units of 0.1° C. As illustrated in FIG. 4, four screw holes 133 are formed in a cooling surface 131A of the contact cooling section 131. The heat conductor 121 is fixed to the contact cooling section 131 by screws 135. In order to enhance the heat conduction efficiency, an indium sheet 137 is interposed between the heat conductor 121 and the contact cooling section 131.

As illustrated in FIGS. 2 to 4, the collecting portion 113 is meanderingly arranged along the cooling surface 131A of the contact cooling section 131. With such arrangement of the collecting portion 113, a larger portion of the collecting portion 113 can be cooled by the contact cooling section 131, and the gas which passes inside the collecting portion 113 can be stabilized. The attitude of installation of SC-UF01 is not limited to that illustrated in FIG. 3, and SC-UF01 may be installed in a laid state. Another advantage of using SC-UF01 and the collecting portion 113 is that SC-UF01 can be in an attitude that matches the location of installation. This is a difference from the conventional preprocessing method which uses a cryogen.

The sealed structure 129 is intended to receive the collecting portion 113, the heat conductor 121, and the contact cooling section 131 of the cooling device 127. The contact cooling section 131 is received inside the sealed structure 129 such that a clearance of about 10 mm is provided between the outer periphery of the contact cooling section 131 and the sealed structure 129 and a clearance of about 10 mm is provided between the upper and lower surfaces of the contact cooling section 131 and the sealed structure 129 in the vertical direction. The space defined by such clearances allows evacuation to be completed in a short time, and enables appropriate heat insulation.

As illustrated in FIG. 3, the sealed structure 129 is constituted from two members, namely the lower structure 139 and the upper structure 141. As illustrated in FIGS. 5A to 5C, the lower structure 139 has a cylindrical shape, and is provided with a flange 139A to be fixed to the cooling device 127 at one end portion and a flange 139B to be fixed to the upper structure 141 at the other end portion. The flange 139B is provided with two groove portions 143A and 143B configured to receive a part of a pipe that connects to the gas pipe (see FIG. 2) made of stainless steel and forming the collecting portion 113. The flange 139B has four screw holes 145 formed therein for fixation of the upper structure 141.

As illustrated in FIGS. 6A to 6C, the upper structure 141 is a lid-like member having an opening at one end portion and a bottom at the other end portion and configured to block the other end portion of the lower structure 139. A flange 141A to be fixed to the flange 139B of the lower structure 139 is provided at the opening end portion of the upper structure 141. The flange 141A has screw holes 147 formed therein at positions corresponding to the screw holes 145. A bottom portion 141B of the upper structure 141 has a vacuum pump connection hole 149 formed therein for connection to the vacuum pump when evacuating the sealed structure 129.

To constitute a vacuum chamber, a flange portion 128 (FIG. 3) of the cooling device 127 and the flange 139A of the lower structure 139 are fixed to each other by a vacuum clamp (not illustrated) with an O-ring interposed therebetween, and the flange portion 139B of the lower structure 139 and the flange 141A of the upper structure 141 are fixed to each other by screws (not illustrated) with an O-ring interposed therebetween. Thus, the sealed structure 129 is obtained. The sealed structure 129 is evacuated using a vacuum pump. With this configuration, the collecting portion 113, the heat conductor 121, and the contact cooling section 131 of the cooling device 127 are thermally insulated from the outside, which enables the collecting portion 113 to be efficiently cooled.

Figure 7A:
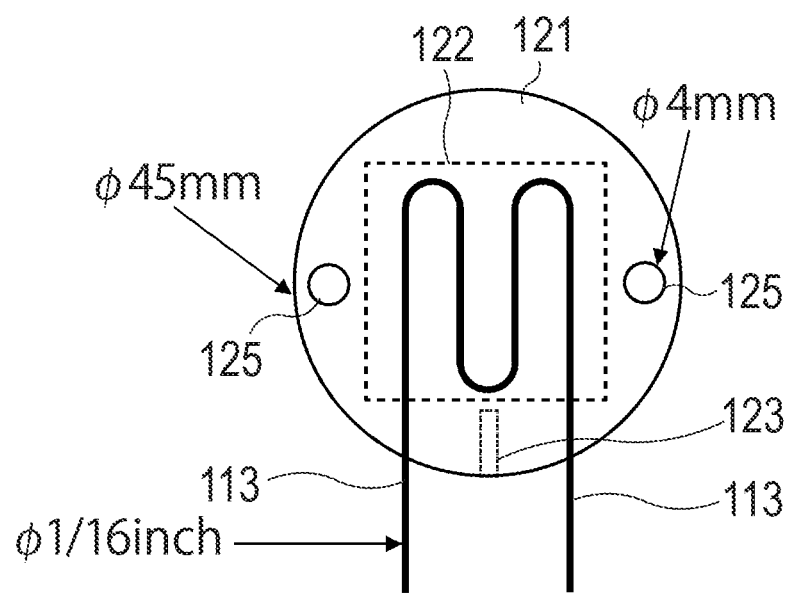
FIGS. 7A and 7B are a plan view and a front view, respectively, illustrating the collecting portion, the heat conductor, and the heater with the heater and the heat conductor being rendered transparent.
Figure 7B:
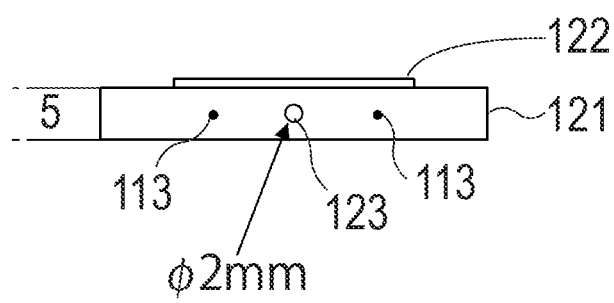

FIGS. 7A and 7B illustrate an example configuration in which the heat conductor 121 is provided with a heater 122. A cable connected to a power source etc. is not illustrated. In FIG. 7A, only the outline of the heater 122 is schematically indicated by broken lines. The heater 122 is a sheet-like heater, and is configured to be electrically energized to generate heat. The heater 122 is provided on a surface of the heat conductor 121 opposite to the surface which contacts the contact cooling section 131. It is optional whether or not to provide the heater 122. The heater 122 is useful if it is desirable to quickly raise the temperature of the collecting portion.

[Gas Generating Source]

In the embodiment, the gas generating source 107 is configured such that phosphoric acid can be dropped into a container that contains a sample. Phosphoric acid is dropped onto the sample to generate a mixed gas. In this embodiment, shells or a part of bones containing calcium carbonate ($CaCO_3$) are used as the sample. When phosphoric acid is dropped onto the sample, a mixed gas containing carbon dioxide ($CO_2$), water ($H_2O$), and a minute amount of other gases is generated. $CO_2$ is the target gas to be analyzed. $H_2O$ (and the minute amount of other gases) is the gas of impurities.

[Flowchart of Process Until Target Gas to be Analyzed is Introduced into Gas Analysis Device]

Figure 8:
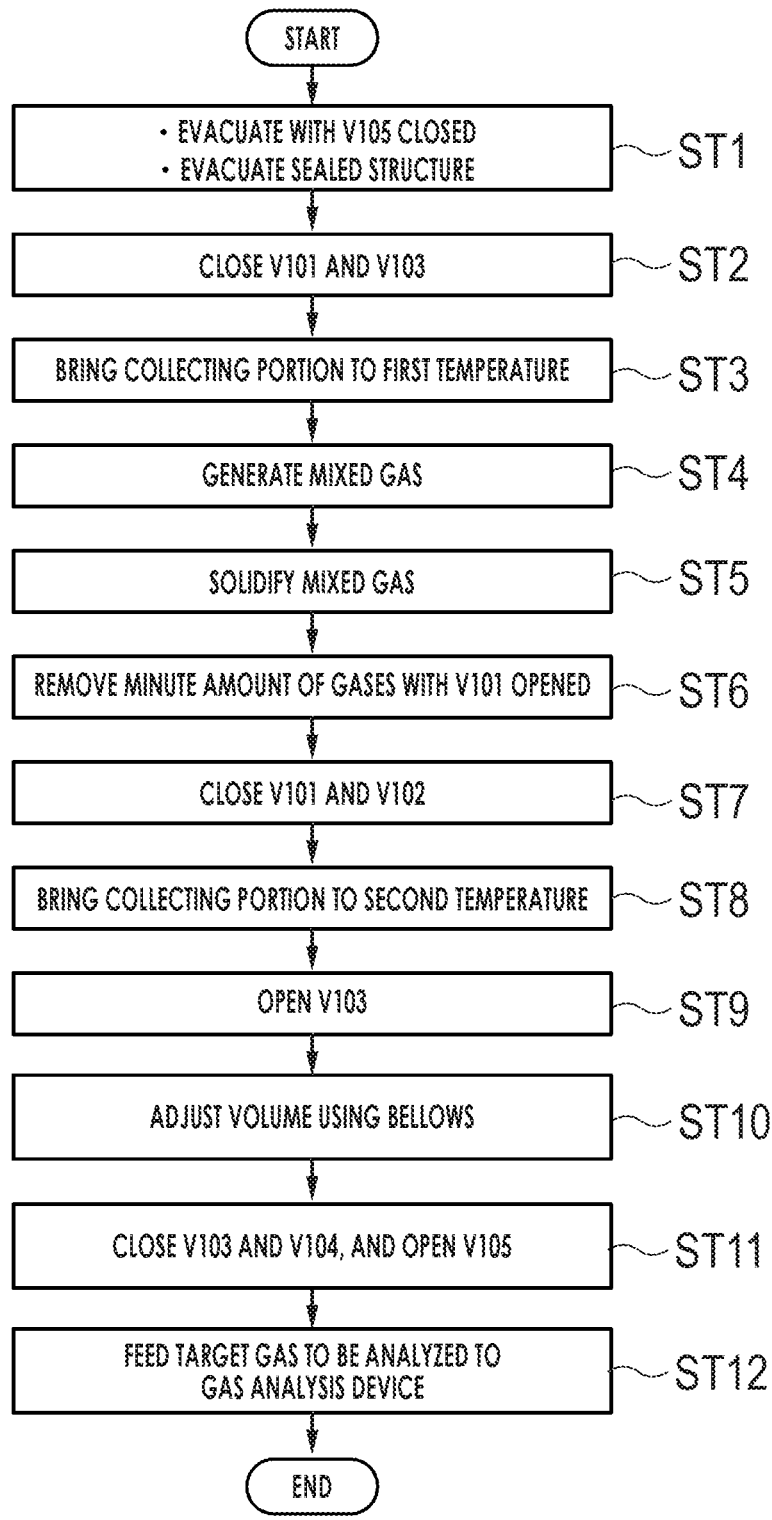
FIG. 8 is a flowchart according to the embodiment of a process until a target gas to be analyzed is introduced into a gas analysis device.

FIG. 8 is a flowchart of a process until the target gas to be analyzed is introduced into the gas analysis device 111. To introduce the target gas into the gas analysis device 111, first, the gas flow path 103 is evacuated using the vacuum pump 109, with only the valve V105 being closed, to establish a vacuum (low to middle vacuum) state. In addition, the sealed structure 129 is evacuated to establish a vacuum (low to middle vacuum) state (step ST1). Then, the valves V101 and V103 are closed (step ST2), and the collecting portion 113 is brought to a first temperature using the cooling device 127 (step ST3). The first temperature may be a temperature at which $CO_2$ as the target gas is solidified (a temperature lower than the sublimation point). In the embodiment, $CO_2$ is cooled to −196° C. as in the conventional preprocessing method. In this embodiment, the gas flow path 103 has been evacuated to about 0 to 5 Torr (1.013 bar to 1.019 bar), and therefore the sublimation point is slightly lower than −78.5° C. that is the sublimation point at normal pressure.

When the gas generating source 107 generates a gas (mixed gas) (step ST4), a pressure gradient is caused between the gas generating source 107 and the collecting portion 113 which has been cooled, and the generated mixed gas is collected in the collecting portion 113 and solidified (step ST5). Specifically, $CO_2$ is solidified into dry ice, and $H_2O$ is solidified into ice. The minute amount of other gases that cannot be collected at this point is removed utilizing the vacuum pump 109 with the valve V101 being opened (step ST6). After that, the valves V101 and V102 are closed (step ST7).

Next, the collecting portion 113 is brought to a second temperature using the cooling device 127. The second temperature may be a temperature around or higher than the temperature at which $CO_2$ is gasified (sublimation point). In the embodiment, the temperature is raised to −80° C. as in the conventional preprocessing method. If the heater 122 is provided, the heater 122 is actuated to quickly raise and adjust the temperature. To measure a sample containing much water, it is preferable to set the temperature to be low in order to remove as much water ($H_2O$) as possible. Therefore, it is desirable to adjust the second temperature according to the state of the sample or the like. When the temperature of the collecting portion 113 is raised to the second temperature, $CO_2$ alone is gasified with $H_2O$ remaining in an ice state. After that, the valve V103 is opened (step ST9) to measure the amount of generated $CO_2$ using the pressure gauge 117. The volume of the bellows 115 is adjusted so as to achieve a predetermined pressure (step ST10). The valves V103 and V104 are closed and the valve V105 is opened (step ST11). The target gas to be analyzed is diffused to feed the target gas to the gas analysis device 111 (step ST12).

In the embodiment, it is not necessary to use liquid nitrogen. Therefore, it is not necessary to use a glass pipe or a stainless steel pipe having a large diameter, and the collecting portion 113, in particular, can be formed from a gas pipe that is made of a stainless steel alloy and that is thin and short compared to the conventional glass pipe as discussed above. Therefore, the space in the collecting portion 113 is small, which makes it possible to make the target gas thick compared to the related art. The target gas having a sufficient concentration can be obtained even if the step of concentrating the target gas is not performed before the target gas is fed to the gas analysis device. As a matter of course, this does not mean to exclude the concentration step, and the concentration step may be performed depending on the analysis content or the like.

While an exemplary embodiment of the present invention has been specifically described above, the present invention is not limited to such an embodiment, and it is a matter of course that changes, modifications, or variations may be made within the scope of the technical concept of the present invention. For example, the present invention can also be used when an organic matter is used as a sample, a silica glass pipe containing the organic matter is evacuated and then sealed to prepare a sealed pipe, the sealed pipe is burnt to generate a mixed gas containing $CO_2$, water, $NO_R$, and $SO_x$, and $NO_x$ and $SO_x$ containing water as gases of impurities are removed. This method is used in a radiocarbon isotope dating method that is widely used in archeology and geology. In this method, it is necessary to prepare high-purity $CO_2$ from which impurities have been completely removed, and to prepare graphite from the high-purity $CO_2$. In this case, the first temperature and the second temperature for the cooling device 127 may be set to −196° C. and −130° C., respectively, since $NO_x$ and $SO_x$ can be trapped when cooled to −130° C.

The target gas to be analyzed and the gases of impurities are separated from each other utilizing the solidification temperatures of the respective gases and the temperatures at which the gases are gasified from a solid state. Therefore, even if one of the gases of impurities has the lowest solidification temperature or a plurality of gases of impurities are mixed, the target gas can be extracted by setting corresponding temperature levels. For example, the target gas is $CO_2$ in the above embodiment. If the target gas is water, the collecting portion can be cooled stepwise to a plurality of temperature levels. For example, the mixed gas is cooled to a first temperature at which $CO_2$ can be solidified, thereafter $CO_2$ is gasified at a second temperature higher than the first temperature, then $CO_2$ is discharged using a pump, and thereafter the temperature is raised to a third temperature of 0° C. or higher to obtain only water.

The present invention is also applicable to implement the "purge and trap" method which is used in volatile gas analysis. In the "purge and trap" method, a sample set in a thermal desorption portion is heated under an inert gas (helium), and a generated gas component is adsorbed by a trap pipe (collecting portion) that has been cooled. Next, the trap pipe is rapidly heated, and the adsorbed gas is introduced into a gas chromatograph for gas chromatography or the like. The trap pipe (collecting portion) may be cooled and heated using a device that is similar to the preprocessing apparatus for gas analysis according to the embodiment described above.

INDUSTRIAL APPLICABILITY

According to the present invention, it is possible to perform preprocessing for gas analysis, in which a target gas to be analyzed is extracted, without using a cryogen. In addition, a target gas to be analyzed that has a sufficient concentration can be obtained even without performing a step of concentrating the target gas to be analyzed.

DESCRIPTION OF REFERENCE NUMERALS

101 preprocessing apparatus for gas analysis
103 gas flow path
105 cooling portion
107 gas generating source
109 vacuum pump
111 gas analysis device
113 collecting portion
115 bellows
117 pressure gauge
121 heat conductor
123 temperature sensor insertion hole
125 through hole
127 cooling device
129 sealed structure
131 contact cooling section
133 screw hole
135 screw
137 indium sheet
139 lower structure
141 upper structure
143 groove portion
145 through hole
147 through hole
149 vacuum pump connection hole

The invention claimed is:

1. A preprocessing apparatus for gas analysis comprising:
a gas flow path including a collecting portion that is cooled to a plurality of temperature levels in order to separate a gas having the lowest solidification temperature, as a target gas to be analyzed, from a mixed gas containing a plurality of kinds of gases and to collect other kinds of gases other than the target gas, as gases of impurities;
a cooling device operable to cool the collecting portion of the gas flow path to the plurality of temperature levels;
a gas flow path connection changing means for connecting the gas flow path to a vacuum pump when evacuating the gas flow path, connecting the gas flow path to a gas generating source when introducing the mixed gas into the gas flow path after the gas flow path has been evacuated, and connecting the gas flow path to a gas analysis device in order to supply the target gas to be analyzed, which has been separated by the collecting portion, to the gas analysis device; and a heat conductor configured to surround an outer periphery of the collecting portion, wherein the cooling device includes a contact cooling section configured to contact the heat conductor to uniformly cool the collecting portion to a set temperature, and has a temperature adjusting function of adjusting a temperature of the contact cooling section to an arbitrary temperature by utilizing electrical energy;

the collecting portion, the heat conductor, and the contact cooling section are received in a vacuum chamber of a sealed structure, the vacuum chamber being connected to a vacuum pump and evacuated; and, the vacuum chamber has been brought into a vacuum state by the vacuum pump when the collecting portion is cooled.

2. The preprocessing apparatus for gas analysis according to claim 1, wherein
the heat conductor contacts the contact cooling section via an indium sheet.

3. The preprocessing apparatus for gas analysis according to claim 2, wherein
the collecting portion is meanderingly arranged along a cooling surface of the contact cooling section.

4. The preprocessing apparatus for gas analysis according to claim 2, wherein
the collecting portion has an overall length of 5 cm or more and 15 cm or less.

5. The preprocessing apparatus for gas analysis according to claim 2, wherein
the collecting portion has a diameter of one-eighth of an inch (3.175 mm) or less.

6. The preprocessing apparatus for gas analysis according to claim 1, wherein
the collecting portion is meanderingly arranged in the heat conductor.

7. The preprocessing apparatus for gas analysis according to claim 1, wherein:
the collecting portion is a gas pipe through which the mixed gas flows; and
the heat conductor is insert molded including the gas pipe as an insert.

8. The preprocessing apparatus for gas analysis according to claim 1, wherein
the heat conductor includes a heater configured to be electrically energized to generate heat.

9. The preprocessing apparatus for gas analysis according to claim 1, wherein:
the mixed gas is a gas generated by adding phosphoric acid to a sample;
a main component of the impurities is water; and
the target gas to be analyzed is carbon dioxide.

10. A preprocessing apparatus for gas analysis comprising:
a gas flow path including a collecting portion that is cooled to a plurality of temperature levels in order to separate a plurality of kinds of gases contained in a mixed gas into a target gas to be analyzed and gases of impurities;
a cooling device operable to cool the collecting portion of the gas flow path to the plurality of temperature levels;
a gas flow path connection changing means for connecting the gas flow path to a vacuum pump when evacuating the gas flow path, connecting the gas flow path to a gas generating source when introducing the mixed gas into the gas flow path after the gas flow path has been evacuated, and connecting the gas flow path to a gas analysis device in order to supply the target gas to be analyzed, which has been separated by the collecting portion, to the gas analysis device; and a heat conductor configured to surround an outer periphery of the collecting portion, wherein the cooling device includes a contact cooling section configured to contact the heat conductor to uniformly cool the collecting portion to a set temperature, and has a temperature adjusting function of adjusting a temperature of the contact cooling section to an arbitrary temperature by utilizing electrical energy;

the collecting portion, the heat conductor, and the contact cooling section are received in a vacuum chamber of a sealed structure, the vacuum chamber being connected to a vacuum pump and evacuated; and, the vacuum chamber has been brought into a vacuum state by the vacuum pump when the collecting portion is cooled.

11. The preprocessing apparatus for gas analysis according to claim 10, wherein:
the collecting portion, the heat conductor, and the contact cooling section are received in a vacuum chamber of a sealed structure, the vacuum chamber being connected to a vacuum pump and evacuated; and
the vacuum chamber has been brought into a vacuum state by the vacuum pump when the collecting portion is cooled.

12. The preprocessing apparatus for gas analysis according to claim 10, wherein
the heat conductor contacts the contact cooling section via an indium sheet.

13. The preprocessing apparatus for gas analysis according to claim 10, wherein
the collecting portion is meanderingly arranged in the heat conductor.

14. The preprocessing apparatus for gas analysis according to claim 10, wherein:
the collecting portion is a gas pipe through which the mixed gas flows; and
the heat conductor is insert molded including the gas pipe as an insert.

15. A preprocessing apparatus for gas analysis comprising:
a gas flow path including a collecting portion that is cooled in order to collect a target gas to be analyzed;
a cooling device operable to cool the collecting portion of the gas flow path; and
a heat conductor configured to surround an outer periphery of the collecting portion, wherein
the cooling device includes a contact cooling section configured to contact the heat conductor to uniformly cool the collecting portion to a set temperature, and has a temperature adjusting function of adjusting a temperature of the contact cooling section to an arbitrary temperature by utilizing electrical energy;
the collecting portion, the heat conductor, and the contact cooling section are received in a vacuum chamber of a sealed structure, the vacuum chamber being connected to a vacuum pump and evacuated; and,
the vacuum chamber has been brought into a vacuum state by the vacuum pump when the collecting portion is cooled.

16. The preprocessing apparatus for gas analysis according to claim 15, wherein:

the collecting portion, the heat conductor, and the contact cooling section are received in a vacuum chamber of a sealed structure, the vacuum chamber being connected to a vacuum pump and evacuated; and the vacuum chamber has been brought into a vacuum state by the vacuum pump when the collecting portion is cooled.

17. The preprocessing apparatus for gas analysis according to claim 15, wherein the heat conductor contacts the contact cooling section via an indium sheet.

18. The preprocessing apparatus for gas analysis according to claim 15, wherein the collecting portion is meanderingly arranged in the heat conductor.

19. The preprocessing apparatus for gas analysis according to claim 15, wherein:

the collecting portion is a gas pipe through which the mixed gas flows; and the heat conductor is insert molded including the gas pipe as an insert.

* * * * *